United States Patent [19]

Frederick

[11] Patent Number: 4,674,483

[45] Date of Patent: Jun. 23, 1987

[54] SHOULDER RETRACTION DEVICE

[76] Inventor: Philip R. Frederick, 632 - 17th Ave., Salt Lake City, Utah 84103-3709

[21] Appl. No.: 837,365

[22] Filed: Mar. 7, 1986

[51] Int. Cl.$^4$ .............................................. A61F 5/00
[52] U.S. Cl. ....................................... 128/68; 128/75; 128/78; 269/328
[58] Field of Search .................. 128/71, 75, 78, 84 C, 128/68; 269/328

[56] References Cited

U.S. PATENT DOCUMENTS 3,152,802 10/1964 Heisler et al. ..................... 128/71 X
3,629,581 12/1971 Smith ..................................... 128/75
4,010,744 3/1977 Boyer ..................................... 128/75

Primary Examiner—Edgar S. Burr
Assistant Examiner—Moshe I. Cohen
Attorney, Agent, or Firm—Thorpe, North & Western

[57] ABSTRACT

Shoulder retraction apparatus for use on a table on which a patient is lying. The apparatus includes a base plate for placement under the patient's legs, a footboard attached to the baseplate near the rearward end thereof to extend upwardly, a pair of shoulder slings formed of loops of material to fit over the shoulders of the patient, and ties for connecting the shoulder slings to the footboard to pull the shoulders toward the footboard under tension.

8 Claims, 2 Drawing Figures

SHOULDER RETRACTION DEVICE

BACKGROUND OF THE INVENTION

This invention relates to a shoulder retraction device especially adapted for use in radiographic examination of a patient.

Radiographic examination of patients typically requires that the shoulders of the patient be maintained in a "low" position. If the patient is examined in a sitting or standing position, gravity will typically maintain the shoulders in a reasonably "low" position. Occasionally, patients are given weights to hold to draw the shoulders to an even lower position and thus avoid shoulder obscuration of the lower cervical spine. However, when patients must be examined in the horizontal or supine position such as for computed tomography of the cervical spine or for conventional radiography of those who are unconscious, a mechanism is needed to hold the shoulders in a "low" position to permit visualization of the lower part of the cervical spine. Tradionally, this has been done by placing another person at the foot of the table on which the patient is lying and having the person pull downwardly on the wrist of the patient during examination. This procedure is not possible, however, for all radiographic examinations such as for computed tomography since multiple images are typically required over many minutes during which time the patient should have no movement whatever.

A number of devices have been utilized by which a patient's wrists are pulled downwardly during examination. These devices are quite uncomfortable since they constrict the wrist and occasionally damage nerves and veins.

SUMMARY OF THE INVENTION

It is an object of the invention to provide a shoulder retraction device for maintaining the shoulders of a patient lying in the horizontal position in a "low" position for radiographic examination.

It is another object of the invention to provide such a device which is comfortable to the patient and will not cause injury of damage.

The above and other objects of the invention are realized in a specific illustrative embodiment of shoulder retraction apparatus which includes a base plate for placement under a patient's legs, a footboard attached to the base plate near a rearward end to extend upwardly therefrom, a pair of shoulder slings each formed of a loop of material to fit over a respective shoulder of the patient, and a tie arrangement for connecting the loops to the footboard to pull the shoulders of a patient toward the footboard when the shoulder slings are in place on a patient and the patient's legs and feet are resting on the base plate and footboard respectively.

In accordance with one aspect of the invention, the tie arrangement includes a mechanism mounted on the footboard for varying the tension under which the shoulder slings are pulled toward the footboard.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
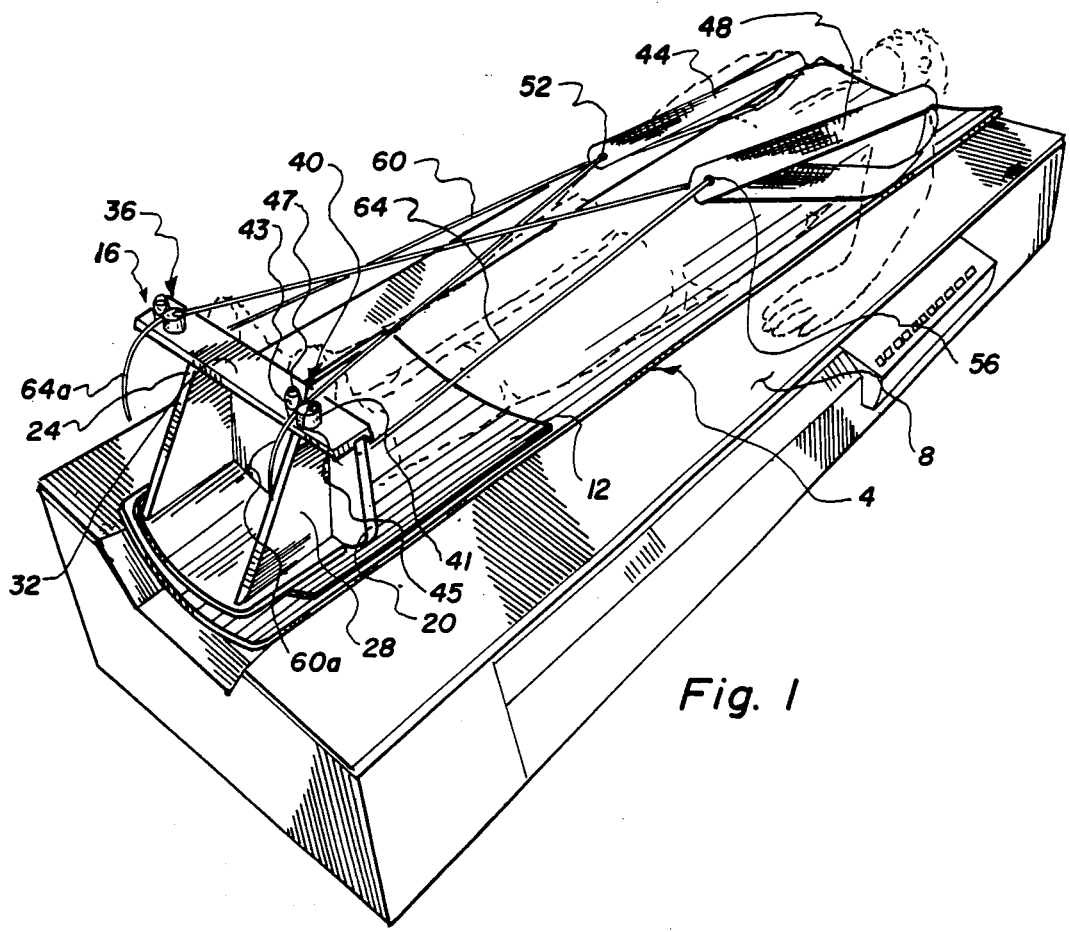
FIG. 1 shows a perspective view of shoulder retraction apparatus applied to a patient lying on a computed tomography table.
Figure 2:
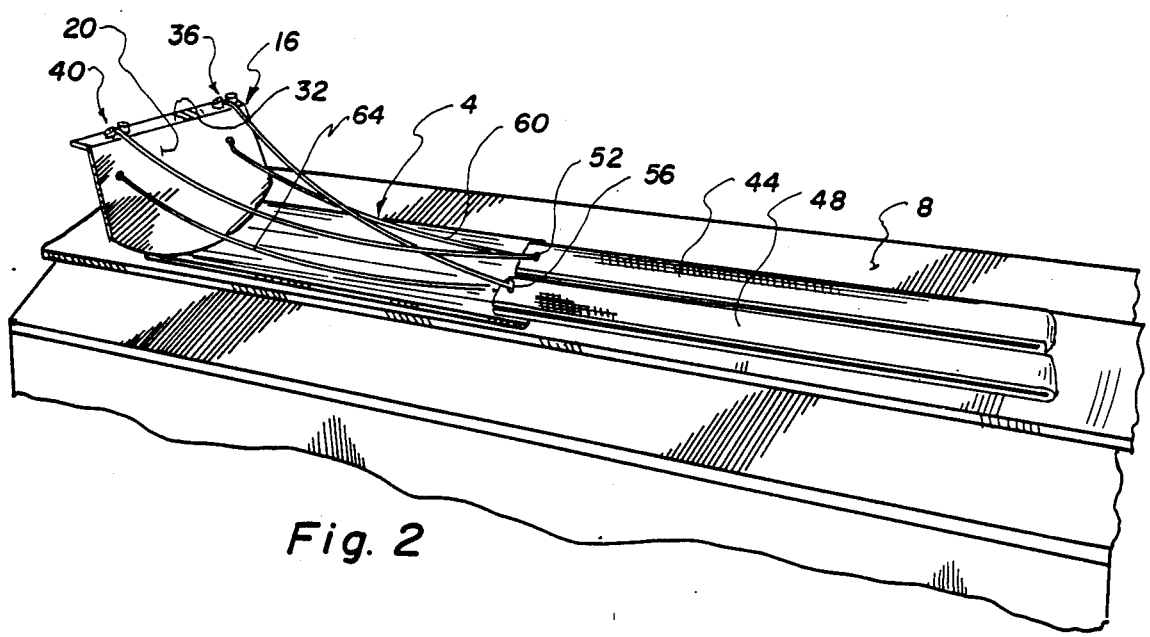
FIG. 2 shows the apparatus with the shoulder slings and ties lying in a ready to use position on the table.

Referring to the drawings, there is shown a shoulder retraction apparatus 4 made in accordance with the present invention and placed on a computed tomography table 8. The apparatus includes a base plate 12 made, for example, of a thin metallic sheet of material and having an upper surface which is generally concave in the transverse direction. Shaping the base plate 12 in this fashion provides for rigidity in the longitudinal direction.

Mounted at the lower or rearward end of the base plate 12 to extend upwardly therefrom is a footboard assembly 16. The footboard assembly 16 is attached to the upper surface of the base plate 12 and includes a generally flat primary section or footplate 20 disposed transversely on the baseplate 12 to project upwardly therefrom so that one face of the footplate faces forwardly and the other faces rearwardly. The footplate 20 extends substantially the entire width of the baseplate 12 as shown. A pair of braces 24 and 28 attached to the rear face of the footplate 20 to extend rearwardly thereof in a generally parallel relationship with one another. Front edges of the braces 24 and 28 are attached to the rear face of the footplate 20 and lower edges of the braces are attached to the upper surface of the base plate 12. The braces 24 and 28 and footplate 20 may be made of wood, plastic, metal or similar material and may be attached to the baseplate 12 and together with screws or other fastening elements.

Disposed on the upper edge of the footplate 20 is a mounting board 32 on which are mounted a pair of conventional cam cleats 36 and 40. Each of the cleats includes a pair of generally cylindrical, spring loaded barrels or wheels (identified by numerals 41 and 43 for cleat 40) whereby the barrels are allowed to turn in one direction only. The perimeter of each barrel of the cleats includes serrations to better grip a tether or rope to be inserted in each cleat between respective barrels. A tether is inserted into and removed from a cleat by forcing it downwardly between the barrels and pulling it upwardly from between the barrels. These mechanisms are well understood.

The shoulder retraction apparatus 4 also includes a pair of slings 44 and 48, each formed of a strip of rugged cloth material, such as canvas, nylon, dacron, or the like, folded so that the ends are positioned together. The ends of each sling 44 and 48 include eyelets 52 and 56 through which is threaded respective ropes or tethers 60 and 64 respectively. One end of the tether 60 is held in place near a side edge of the footplate 20 (for example by inserting the tether through an opening in the footplate and then tying a knot in the end to prevent it from slipping back through the hole) while the other end of the tether is threaded through the eyelets 52 and back to cam cleat 40 which secures the tether under tension. Tether 64 similarly is positioned so that one end thereof is held in place near the opposite side edge of the footplate 20 while the other end is threaded through eyelets 56 and back to cam cleat 36.

The shoulder retraction apparatus is used by placing a patient's legs on the base plate 12 as shown in FIG. 1, with the patient's feet resting against the footplate 20.

The shoulder slings 44 and 48 are then placed or looped about respective shoulders with the ends of the slings directed towards the footboard 16 as shown in FIG. 1. With the tether 60 and 64 in place on the footboard assembly 16 and looped through the eyelets 52 and 56, ends 60a and 64a are pulled through the cam cleats 40 and 36 respectively downwardly from the patient until the appropriate tension has been applied to the shoulder slings 44 and 48. The barrels of the cleats rotate in one direction as the tethers are pulled through the cleats, but are prevented from rotating in the opposite direction. In this way, the tethers are firmly secured. With the shoulders of the patient in the proper "lowered" position, the radiographic examination can proceed.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Shoulder retraction apparatus comprising a base plate for placement under a patient's legs, said plate having a forward end and a rearward end, a footboard attached at one edge thereof to the base plate near the rearward end to extend upwardly therefrom, said footboard having a generally forwardly facing surface against which a patient's feet may be placed, a pair of shoulder slings, each formed of a loop of material to fit over a respective shoulder of a patient, tie means for connecting the loops of material individually to the footboard to pull the shoulders of a patient toward the footboard when the shoulder slings are in place on a patient and the patient's legs and feet are resting on the base plate and footboard respectively, and means for securing the tie means to the footboard under tension.

2. Apparatus as in claim 1 wherein the upper surface of the base plate is concave in the transverse direction.

3. Apparatus as in claim 2 wherein the base plate comprises a thin metallic sheet of material.

4. Apparatus as in claim 1 wherein the footboard comprises a generally flat primary section disposed transversely on the base plate to project upwardly, one face of which faces forwardly and one faces rearwardly, and a brace joined to the rearward facing side of the primary section and to the base plate to support the primary section.

5. Apparatus as in claim 4 wherein the securing means is disposed at or near the top of the primary section to secure the tie means.

6. Apparatus as in claim 1 wherein said shoulder slings each comprises a strip of material, the ends of which are joined together and include an eyelet through which a tether may be inserted, and wherein said tie means comprises a pair of tethers, each of which is secured at one end to a respective side of the footboard, said each tether being inserted through the eyelet of a respective shoulder sling, with the other end of said each tether being secured to by the securing means to the footboard.

7. Apparatus as in claim 6 wherein said securing means comprises a pair of cam cleats mounted on the footboard, each of which secures a respective other end of said each tether under tension.

8. Apparatus as in claim 6 wherein the shoulder slings are made of canvas, nylon, dacron, or the like.

* * * * *